United States Patent [19]

Lesher et al.

[11] Patent Number: 4,650,806

[45] Date of Patent: Mar. 17, 1987

[54] CARDIOTONIC 5-(HETERYLCARBONYL)-PYRIDONES

[75] Inventors: George Y. Lesher, Schodack; Baldev Singh, Greenbush, both of N.Y.

[73] Assignee: Sterling Drug Inc., New York, N.Y.

[21] Appl. No.: 691,238

[22] Filed: Jan. 14, 1985

[51] Int. Cl.$^4$ .................... A61K 31/44; C07D 409/06; C07D 213/84; C07D 405/06

[52] U.S. Cl. .................................. 514/335; 514/336; 546/261; 546/283; 546/284

[58] Field of Search ....................... 546/283, 284, 261; 514/335, 336

[56] References Cited

U.S. PATENT DOCUMENTS

| | | | |
|---|---|---|---|
| 4,412,077 | 10/1983 | Lesher et al. | 546/298 |
| 4,415,580 | 11/1983 | Lesher et al. | 546/288 X |
| 4,555,517 | 11/1985 | Stout et al. | 514/336 |
| 4,567,186 | 1/1986 | Lesher et al. | 514/300 |
| 4,568,751 | 2/1986 | Jones et al. | 546/297 |

FOREIGN PATENT DOCUMENTS 124090 11/1984 European Pat. Off. ............ 546/261

Primary Examiner—Richard A. Schwartz
Attorney, Agent, or Firm—Robert K. Bair; B. Woodrow Wyatt; Paul E. Dupont

[57] ABSTRACT

3-Z-5-(Q-CO)-6-methyl-2(1H)-pyridinones (I) or salts thereof, where Q is 2(or 3)-furanyl or 2(or 3)-thienyl when Z is hydrogen or cyano, or where Q is 4(or 3)-pyridinyl or 4(or 3)-pyridinyl having one or two methyl substituents only when Z is cyano, are useful as cardiotonic agents. Processes for preparing said compounds (I) are shown.

12 Claims, No Drawings

CARDIOTONIC 5-(HETERYLCARBONYL)-PYRIDONES

CROSS-REFERENCE TO RELATED APPLICATION

Copending application Ser. No. 691,802, filed Jan. 14, 1985, now U.S. Pat. No. 4,567,186 issued Jan. 28, 1986, discloses and claims 5-(aromatic-heteryl)-1,6-naphthyridin-2(1H)-ones, their cardiotonic use, their preparation and intermediates. These 5-(aromatic-heteryl)-1,6-naphthyridin-2(1H)-ones are prepared from 5-[(aromatic-heteryl)carbonyl]-6-methyl-2(1H)-pyridinones which are disclosed and claimed herein.

BACKGROUND OF THE INVENTION (a) Field of the Invention

This invention relates to 5-[(aromatic-heteryl)carbonyl]-6-methyl-2(1H)-pyridinones, their preparation, and their use as cardiotonic agents and intermediates.

(b) Information Disclosure Statement

Lesher and Singh in U.S. Pat. No. 4,415,580, issued Nov. 15, 1983, show as cardiotonic agents 5-(lower-alkyl)-1,6-naphthyridin-2(1H)-ones (I) and their preparation by reacting a 5-(lower-alkanoyl)-6-methyl-2(1H)-pyridinone with di-(lower-alkyl)formamide di-(lower-alkyl)acetal to produce 5-(lower-alkanoyl)-6-[2-(di-lower-alkylamino)ethenyl]-2(1H)-pyridinone (II) and reacting II with formamidine or ammonia or salt thereof to produce I.

Lesher and Singh in U.S. Pat. No. 4,412,077, issued Oct. 25, 1983, show as cardiotonic agents 5-(lower-alkanoyl)-6-(lower-alkyl)-2(1H)-pyridinones (I) and their preparation by reacting 2-(lower-alkanoyl)-1-(lower-alkyl)-ethenamine (II) with a lower-alkyl 2-propynoate.

Copending U.S. patent application Ser. No. 630,810, filed July 13, 1984, now U.S. Pat. No. 4,560,691 issued Dec. 24, 1985, discloses and claims 5-(benzoyl and selected substituted-benzoyl)-6-methyl-2(1H)-pyridinones, their preparation, their use as intermediates for preparing selected 5-(phenyl)-1,6-naphthyridin-2(1H)-ones (cardiotonic agents) and the use of 5-(benzoyl or hydroxybenzoyl)-6-methyl-2(1H)-pyridinone as a cardiotonic agent.

Merrell Dow Pharmaceuticals Inc. (Inventors: Winton D. Jones, Richard A Schnettler and Richard C. Page) European Patent Application No. 124090, published Nov. 7, 1984, filed Apr. 26, 1984 and having a U.S. priority of Apr. 29, 1983 (U.S. application Ser. No. 490,081), now U.S. Pat. No. 4,568,751, has the following generic teaching:

"More specifically, this invention relates to pharmaceutically active 5-acyl-2-(1H)-pyridinones of the formula I

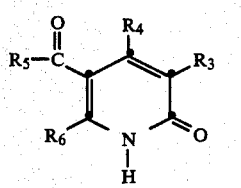

and the pharmaceutically acceptable salts thereof, wherein $R_3$ is H, —C≡N, $NH_2$, $CONH_2$ and COOR with R being hydrogen or lower alkyl, $R_4$ is hydrogen or lower alkyl, $R_5$ is phenyl, X-substituted phenyl, pyridyl, thienyl, furyl, pyrrolyl and OR wherein R is hydroxy or lower alkoxy, and X is lower alkyl, lower alkoxy, lower alkyl thio, halogen, nitro, lower alkanoyl, alkoxy carbonyl, carboxy, cyano, $NH_2$, $CONH_2$, amidino, imidazol-2-yl, and $CF_3$, and $R_6$ is hydrogen, methyl, ethyl or $R_5$. These compounds are useful as cardiotonics in the treatment of cardiac failure and other conditions requiring strengthening of heart action with a cardiotonic agent." Compounds specifically disclosed are all nicotinonitriles, that is, compounds of formula I where $R_3$ is cyano. Included among these nicotinonitriles are: 5-($R_5$CO)-6-ethyl-2-oxo-1,2-dihydro-3-pyridinecarbonitriles where $R_5$ is 4-pyridinyl, 2-thienyl and 3-furanyl, "and the 6-methyl homologs thereof." Illustrative of the preparation of these compounds is the reaction of 1-benzoylacetone with dimethylformamide dimethyl acetal to produce 2-[(dimethylamino)methylene]-1-phenyl-1,3-butanedione (Ex. 1) and reaction of the dione with cyanoacetamide in the presence of sodium hydride in tetrahydrofuran to produce 5-acetyl-1,2-dihydro-2-oxo-6-phenyl-3-pyridinecarbonitrile. Specifically named intermediate 2-[(dimethylamino)methylene]-1-$R_5$-1,3-butanediones include those where $R_5$ is 4-pyridinyl, 2-thienyl and 3-furanyl.

SUMMARY OF THE INVENTION

In a composition of matter aspect the invention resides in 3-Z-5-(Q-CO)-6-methyl-2(1H)-pyridinone having the formula I

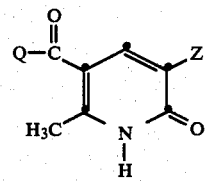

or cationic salt thereof, where Q is 2(or 3)-furanyl or 2(or 3)-thienyl when Z is hydrogen or cyano or where Q is 4(or 3)-pyridinyl or 4(or 3)-pyridinyl having one or two methyl substituents only when Z is cyano, or acid-addition salt thereof where Q is 4(or 3)-pyridinyl or 4(or 3)-pyridinyl having one or two methyl substituents. The compounds of formula I are useful as cardiotonic agents, as determined by standard pharmacological evaluation procedures and, also, are useful as intermediates in preparing 3-Z-5-Q-1,6-naphthyridin-2(1H)-ones having the formula II

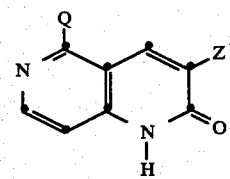

or acid-addition or cationic salt thereof, where Z is hydrogen, cyano or carboxy, and Q is 2(or 3)-furanyl, 2(or 3)-thienyl, 4(or 3)-pyridinyl or 4(or 3)-pyridinyl having one or two methyl substituents. The compounds of formula II where Z is hydrogen or cyano are useful as cardiotonic agents, as determined by standard pharmacological evaluation procedures. The compounds of formula II where Z is carboxy are useful as intermediates for preparing the compounds of formula II where Z is hydrogen. The compounds of formula II are prepared from the compounds of formula I via the 3-Z-5-(Q-CO)-6-[2-(di-lower-alkyl-amino)ethenyl]-2(1H)-pyridinones having the formula III

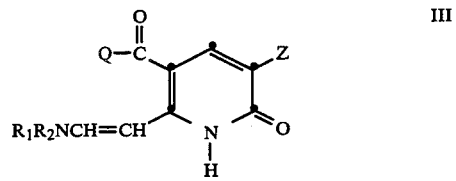

or acid-addition salt thereof, where Q is 2(or 3)-furanyl or 2(or 3)-thienyl when Z is hydrogen or cyano, or Q is 4(or 3)-pyridinyl or 4(or 3)-pyridinyl having one or two methyl substituents only when Z is cyano.

The compounds of formulas II and III, their preparation, and the cardiotonic use of the compounds of formula II are disclosed and claimed in U.S. Pat. No. 4,567,186.

A composition aspect of the instant invention resides in the cardiotonic composition for increasing cardiac contractility which comprises a pharmaceutically acceptable carrier and, as the active component thereof, a cardiotonically effective amount of 3-Z-5-(Q-CO)-6-methyl-2(1H)-pyridinone having the formula I or pharmaceutically acceptable acid-addition or cationic salt thereof.

A method aspect of the invention resides in the method for increasing cardiac contractility in a patient requiring such treatment which comprises administering orally or parenterally in a solid or liquid dosage form to such patient a cardiotonically effective amount of 3-Z-5-(Q-CO)-6-methyl-2(1H)-pyridinone having the formula I or pharmaceutically acceptable acid-addition or cationic salt thereof.

A process aspect of the invention resides in the process which comprises reacting 3-amino-1-Q-2-buten-1-one with a lower-alkyl 2-propynoate to produce 5-(Q-CO)-6-methyl-2(1H)-pyridinone of formula I where Z is hydrogen and Q is 2(or 3)-furanyl or 2(or 3)-thienyl.

Another process aspect of the invention resides in the process which comprises reacting 1-Q-1,3-butanedione with dimethylformamide dimethyl acetal to produce 1-Q-2-[(dimethylamino)methylene]-1,3-butanedione, heating the latter compound with cyanoacetamide in the presence of a basic condensing agent, and acidifying the reaction mixture to produce 1,2-dihydro-2-oxo-5-(Q-CO)-6-methylpyridine-3-carbonitrile having the formula I where Z is cyano and Q is 2(or 3)-furanyl, 2(or 3)-thienyl, 4(or 3)-pyridinyl or 4(or 3)-pyridinyl having one or two methyl substituents.

DETAILED DESCRIPTION INCLUSIVE OF PREFERRED EMBODIMENTS

Preferred compounds having formula I are those where Q is 4(or 3)-pyridinyl when Z is cyano, and where Q is 2(or 3)-furanyl and 2(or 3)-thienyl when Z is hydrogen.

The term "lower-alkyl" as used herein, e.g., as the meaning of $R_1$ or $R_2$ in formula III means alkyl radicals having from 1 to 4 carbon atoms which can be arranged as straight or branched chains, illustrated by methyl, ethyl, n-propyl, isopropyl, n-butyl, sec.-butyl, tert.butyl and isobutyl.

The compounds of formula I where Q is 4(or 3)-pyridinyl or 4(or 3)-pyridinyl having one or two methyl substituents are useful both in the free base form and in the form of acid-addition salts, and, both forms are within the purview of the invention. The acid-addition salts are simply a more convenient form for use; and in practice, use of the salt form inherently amounts to use of the base form. The acids which can be used to prepare the acid-addition salts of said compounds of formula I include preferably those which produce, when combined with the free base, pharmaceutically acceptable salts, that is, salts whose anions are relatively innocuous to the animal organism in pharmaceutical doses of the salts, so that the beneficial cardiotonic properties inherent in the free base are not vitiated by side effects ascribable to the anions. Appropriate pharmaceutically acceptable salts within the scope of the invention are those derived from mineral acids such as hydrochloric acid, hydrobromic acid, sulfuric acid, phosphoric acid and sulfamic acid; and organic acid such as lactic acid, acetic acid, citric acid, tartaric acid, methanesulfonic acid, ethanesulfonic acid, benzenesulfonic acid, p-toluenesulfonic acid, cyclohexylsulfamic acid, quinic acid, and the like, giving the hydrochloride, hydrobromide, sulfate, phosphate, sulfamate, lactate, acetate, citrate, tartrate, methanesulfonate, ethanesulfonate, benzenesulfonate, p-toluenesulfonate, cyclohexylsulfamate and quinate, respectively.

The acid-addition salts of said basic compounds of formula I are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

Although pharmaceutically acceptable salts of said basic compounds of formula I are preferred, all acid-addition salts are within the scope of the invention. All acid-addition salts are useful as sources of the free base form even if the particular salt per se is desired only as an intermediate product as for example when the salt is formed only for purposes of purification or identification, or when it is used as an intermediate in preparing a pharmaceutically acceptable salt by ion exchange procedures.

Other pharmaceutically acceptable salts of said compound of formula I are those cationic salts derived from strong inorganic or organic bases, e.g., sodium hydroxide, potassium hydroxide, trimethylammonium hydroxide, to produce the corresponding cationic salt, e.g., sodium, potassium, trimethylammonium salt, respectively.

The molecular structures of the compounds of formulas I, II and III were assigned on the basis of evidence provided by infrared, ultraviolet, nuclear magnetic resonance and mass spectra, by the correspondence of calculated and found values for the elemental analyses, and by their method of preparation.

The manner of making and using the instant invention will now be generally descibed so as to enable a person skilled in the art of pharmaceutical chemistry to make and use the same.

The 5-(Q-CO)-6-methyl-2(1H)-pyridinone (I where Z is hydrogen) where Q is 2(or 3)-furanyl and 2(or 3)-thienyl is prepared by heating 3-amino-1-Q-2-buten-1-one with a lower-alkyl, preferably methyl or ethyl, 2-propynoate, preferably in a suitable solvent. The reaction is run at about 100° C. to 155° C., preferably in refluxing dimethylformamide. This reaction does not take place where Q is 4(or 3)-pyridinyl or 4(or 3)-pyridinyl having one or two methyl substituents.

The intermediate 3-amino-1-Q-2-buten-1-one where Q is 2(or 3)-furanyl or 2(or 3)-thienyl is conveniently prepared by the generally known procedure of reacting 1-Q-1,3-butanedione with aqueous ammonia in methanol at ambient temperature as illustrated hereinbelow.

The 1,2-dihydro-2-oxo-5-(Q-CO)-6-methylpyridine-3-carbonitrile (I where Z is cyano) is prepared by first reacting (conveniently at room temperature) 1-Q-1,3-butanedione with dimethylformamide dimethyl acetal in the presence of a suitable solvent, e.g., p-dioxane, to produce 1-Q-2-[(dimethylamino)methylene]-1,3-butanedione and heating the latter compound (conveniently in situ) with cyanoacetamide in the presence of an alkali metal lower-alkoxide, preferably sodium methoxide and acidifying the reaction mixture.

The use of the compounds of formula I to prepare the compounds of formula III and II is described in the following paragraphs.

The reaction of 3-Z-5-(Q-CO)-6-methyl-2(1H)-pyridinone (I), with di-(lower-alkyl)formamide di-(loweralkyl) acetal or bis(dimethylamino)-t-butoxymethane to produce 3-Z-5-(Q-CO)-6-[2-(di-lower-alkylamino)ethenyl]-2(1H)-pyridinone (III) is carried out by heating the reactants at about 75° C. to 125° C., preferably about 90° C. to 110° C., and preferably in a suitable inert solvent, e.g., dioxane (p-dioxane) or dimethylformamide. The reaction is preferably run by heating I with dimethylformamide dimethyl acetal preferably in dioxane or in dimethylformamide on a steam bath or by refluxing I with bis(dimethylamino)-t-butoxymethane preferably in dioxane.

The reaction of 3-Z-5-(Q-CO)-6-[2-(di-lower-alkylamino)ethenyl]-2(1H)-pyridinone (III) with formamidine, ammonia or salt thereof, preferably acetate, to produce 3-Z-5-Q-1,6-naphthyridin-2(1H)-one where Q is 2(or 3)-furanyl or 2(or 3)-thienyl when Z is hydrogen or cyano or where Q is 4(or 3)-pyridinyl or 4(or 3)-pyridinyl having one or two methyl substituents only when Z is cyano is carried out by heating the reactants at about 100° C. to 160° C., preferably about 155° C. to 160° C., in a suitable inert solvent, preferably dioxane or dimethylformamide. Preferred salts of formamidine and ammonia are those of weak organic or inorganic acids, for example, acetate, citrate, lactate, tartrate, carbonate, and the like, although salts of strong acids, e.g., hydrochloride and sulfate, also can be used. Optionally, the reaction can be run using ammonia under pressure.

The hydrolysis of 1,2-dihydro-2-oxo-5-Q-1,6-naphthyridine-3-carbonitrile (II where Z is CN) to produce the corresponding 3-carboxylic acid (II where Z is COOH) can be under aqueous acidic or alkaline reaction conditions, preferably by heating II where Z is cyano with 50–90% sulfuric acid or 10–35% aqueous sodium hydroxide solution.

The decarboxylation of 1,2-dihydro-2-oxo-5-Q-1,6-naphthyridine-3-carboxylic acid (II where Z is COOH) to produce the corresponding 5-Q-1,6-naphthyridin-2(1H)-one (II where Z is hydrogen) is carried out by suspending a suitable container containing said 3-carboxylic acid in a high boiling fluid, e.g., a silicone oil, heated to about 340° C. to 380° C.

Disclosed and claimed in copending Applicants U.S. Ser. No. 691,802 are the processes: (a) which comprises reacting 3-Z-5-(Q-CO)-6-methyl-2(1H)-pyridinone having formula I with di-(lower-alkyl)formamide di-(lower-alkyl) acetal or bis(dimethylamino)-t-butoxymethane to produce 3-Z-5-(Q-CO)-6-[2-(di-loweralkylamino)ethenyl]-2(1H)-pyridinone having formula III above, where Q is 2(or 3)-furanyl, 2(or 3)-thienyl when Z is hydrogen or cyano, or Q is 4(or 3)-pyridinyl or 4(or 3)-pyridinyl having one or two methyl substituents only when Z is cyano; b) which comprises reacting 3-Z-5-(Q-CO)-6-[2-(di-lower-alkylamino)ethenyl]-2(1H)-pyridinone of formula III with formamidine or ammonia or salt thereof to produce 3-Z-5-Q-1,6-naphthyridin-2(1H)-one having formula II where Q is 2(or 3)-furanyl or 2(or 3)-thienyl when Z is hydrogen or cyano or where Q is 4(or 3)-pyridinyl or 4(or 3)-pyridinyl having one or two methyl substituents only when Z is cyano; c) which comprises reacting 1,2-dihydro-5-(Q-carbonyl)-6-methyl-2-oxonicotinonitrile with dimethylformamide dimethylacetal to produce 1,2-dihydro-6-[2-(dimethylamino)ethenyl]-5-(Q-carbonyl)-2-oxonicotinonitrile and reacting the latter compound with formamidine, ammonia or salt thereof to produce 1,2-dihydro-2-oxo-5-Q-1,6-naphthyridine-3-carbonitrile, where Q is 2(or 3)-furanyl, 2(or 3)-thienyl), 4(or 3)-pyridinyl or 4(or 3)-pyridinyl having one or two methyl substituents; and, d) which comprises hydrolyzing 1,2-dihydro-2-oxo-5-Q-1,6-naphthyridine-3-carbonitrile to produce 1,2-dihydro-2-oxo-5-Q-1,6-naphthyridine-3-carboxylic acid and decarboxylating the -3-carboxylic acid to produce 5-Q-1,6-naphthyridin-2(1H)-one, where Q is 2(or 3)-furanyl, 2(or 3)-thienyl, 4(or 3)-pyridinyl or 4(or 3)-pyridinyl having one or two methyl substituents.

The following examples will further illustrate the invention without, however, limiting it thereto.

A. 5-(Q-CO)-6-METHYL-2(1H)-PYRIDINONES

A-1. 5-(2-Furanylcarbonyl)-6-methyl-2(1H)-pyridinone—To a stirred solution containing 85 g of 3-amino-1-(2-furanyl)-2-buten-1-one in 500 ml of dimethylformamide was added over a forty minute period 51 g of methyl propiolate (same as methyl 2-propynoate) and the resulting mixture was stirred at ambient temperature for three hours and then refluxed overnight (about fifteen hours). The reaction mixture was then cooled whereupon it set up as a cake. To the cooled reaction mixture was added 200 ml of isopropyl alcohol and the solid was pulverized. The solid was collected, washed with isopropyl alcohol and dried in a vacuum oven at 80°–85° C. to yield 68.4 g of 5-(2-furanylcarbonyl)-6-methyl-2(1H)-pyridinone, m.p. 258°–260° C.

Cationic salts of 5-(2-furanylcarbonyl)-6-methyl-2(1H)-pyridinone are conveniently prepared by reaction with an equivalent quantity of the appropriate base, for example, sodium hydroxide, potassium hydroxide or trimethylammonium hydroxide, to produce the corresponding respective sodium, potassium or trimethylammonium salt. The salts are prepared in solution or in solid form by suspending equivalent quantities of said pyridinone and base in water or water-methanol to form the solution of salt or by evaporating the solvent from the solution to obtain the salt in solid form.

The intermediate 3-amino-1-(2-furanyl)-2-buten-1-one was prepared as follows: A mixture containing 165 g of 1-(2-furanyl)-1,3-butanedione, 700 ml of toluene and 200 g of ammonium acetate was azeotroped for six hours, cooled and concentrated to dryness in vacuo. The residue was dissolved in isopropyl alcohol, the solution treated with decolorizing charcoal and filtered, and the filtrate concentrated to remove the solvent. The remaining residue was recrystallized from ether-ethanol and dried at room temperature to yield 80.2 g of 3-amino-1-(2-furanyl)-2-buten-1-one, m.p. 128°–130° C. Another 33.4 g of the product, m.p. 128°–130° C. was collected by concentrating the mother liquor and extracting the product with ether.

A-2. 6-Methyl-5-(2-thienylcarbonyl)-2(1H)-pyridinone—To a solution containing 16.7 g of 3-amino-1-(2-thienyl)-2-buten-1-one dissolved in 75 ml of dimethylformamide was added dropwise with stirring over a 10–15 minute period 9.8 ml of methyl propiolate. The reaction mixture was stirred at room temperature for 3 and ½ hours and then refluxed for 24 hours. On cooling the reaction mixture there separated a solid which was collected, washed with methanol and dried in a vacuum oven at 90° C. to yield 10.5 g of 6-methyl-5-(2-thienylcarbonyl)-2(1H)-pyridinone, m.p. 227°–228° C.

Cationic salts of 6-methyl-5-(2-thienylcarbonyl)-2(1H)-pyridinone are conveniently prepared as in Example A-1 by reaction with an equivalent quantity of the appropriate base, for example, sodium hydroxide, potassium hydroxide or trimethylammonium hydroxide, to produce the corresponding respective sodium, potassium or trimethylammonium salt.

The intermediate 3-amino-1-(2-thienyl)-2-buten-1-one was prepared as follows: A mixture containing 153 g of 1-(2-thienyl)-1,3-butanedione, 176.7 g of ammonium acetate and 1 liter of toluene was azeotroped for five hours and then allowed to cool. The solid that separated from the reaction mixture was collected, washed successively with toluene and ether, and dried in a vacuum oven at 90° C. to yield 122 g of 1-(2-thienyl)-1,3-butanedione, m.p. 167°–171° C. A 10 g sample of this material was dissolved in 300 ml of boiling toluene, the solution treated with decolorizing charcoal and filtered, and the filtrate allowed to cool. The solid that separated was collected and dried in a vacuum oven at 90° C. to yield 5.8 g of 3-amino-1-(2-thienyl)-2-buten-1-one, as off-white needles, m.p. 170°–172° C. The main portion of the product was then dissolved in boiling isopropyl alcohol, the hot solution treated with decolorizing charcoal and filtered, and the filtrate allowed to cool. The solid that crystallized was collected, washed with isopropyl alcohol, dried in a vacuum oven at 80° C. to yield 74.1 g of product melting at 169°–171° C.

Following the procedure described in Example A-1 using in place of 1-(2-furanyl)-1,3-butanedione a molar equivalent quantity of the appropriate 1-Q-1,3-butanedione, it is contemplated that the 5-(Q-carbonyl)-6-methyl-2(1H)-pyridinones of Examples A-3 and A-4 can be obtained.

A-3. 5-(3-Furanylcarbonyl)-6-methyl-2(1H)-pyridinone, using 3-amino-1-(3-furanyl)-2-buten-1-one.

A-4. 6-Methyl-5-(3-thienylcarbonyl)-2(1H)-pyridinone, using 3-amino-1-(3-thienyl)-2-buten-1-one.

B.
1,2-DIHYDRO-5-(Q-CO)-6-METHYL-2-OXO-NICOTINONITRILES

B-1. 1,2-Dihydro-2-oxo-6-methyl-5-(4-pyridinylcarbonyl)-3-pyridinecarbonitrile—A mixture containing 40 g of 1-(4-pyridinyl)-1,3-butanedione, 100 ml of p-dioxane and 40 ml of dimethylformamide dimethyl acetal was allowed to stand at room temperature for three days (over the weekend) and then concentrated on a rotary evaporator to yield 56.5 g of a dark oily material containing 2-[(dimethylamino)methylene]-1-(4-pyridinyl)-1,3-butanedione. The dark oily material was dissolved in 400 ml of methanol in a 500 ml 3-necked round bottom flask and to the solution was added with stirring 23 g of cyanoacetamide followed by slow addition of 27 g of sodium methoxide preferably using a Gooch tube to avoid contact with moisture. The resulting exothermic reaction was allowed to proceed at ambient temperature for about one hour, next refluxed for four hours and then allowed to stand at room temperature overnight. To the reaction mixture was added 40 ml of glacial acetic acid and the mixture concentrated on a rotary evaporator. To the residue was added 200 ml of methanol and the mixture was allowed to stand at room temperature for about five hours whereupon a solid separated. The solid was collected, washed with methanol and dried to yield 13.2 g of product A. The mother liquor was concentrated, treated with 200 ml of glacial acetic acid and the acidic solution refluxed overnight and cooled. The separated solid was collected, washed with methanol and dried to yield 13.7 g of product B. Product A was recrystallized from dimethylformamide and dried in a vacuum oven in at 90°–95° C. to yield 6.2 g of 1,2-dihydro-2-oxo-6-methyl-5-(4-pyridinylcarbonyl)-3-pyridinecarbonitrile, m.p. >305° C. Product B was recrystallized from dimethylformamide and dried in a vacuum oven at 90°–95° C. to yield 11.4 g of 5-acetyl-1,2-dihydro-2-oxo-6-(4-pyridinyl)-3-pyridinecarbonitrile, m.p. 255°–257° C.

Acid-addition salts of 1,2-dihydro-2-oxo-6-methyl-5-(4-pyridinylcarbonyl)-3-pyridinecarbonitrile are conveniently prepared by adding to a mixture of 2 g of 1,2-dihydro-2-oxo-6-methyl-5-(4-pyridinylcarbonyl)-3-pyridinecarbonitrile in about 40 ml of aqueous methanol the appropriate acid, e.g. methanesulfonic acid, concentrated sulfuric acid, concentrated phosphoric acid, to a pH of about 2 to 3, chilling the mixture after partial evaporation and collecting the precipitate, e.g., dimethanesulphonate, sulphate, phosphate, respectively. Also, the acid-addition salt is conveniently prepared in aqueous solution by adding to water with stirring molar equivalent quantities of 1,2-dihydro-2-oxo-6-methyl-5-(4-pyridinylcarbonyl)-3-pyridinecarbonitrile and the appropriate acid, e.g., lactic acid or hydrochloric acid, to prepare respectively the monolactate or monohydrochloride salt in aqueous solution.

Cationic salts of 1,2-dihydro-2-oxo-6-methyl-5-(4-pyridinylcarbonyl)-3-pyridinecarbonitrile are conveniently prepared as in Example A-1 by reaction with an equivalent quantity of the appropriate base, for example, sodium hydroxide, potassium hydroxide or trimethylammonium hydroxide, to produce the corresponding respective sodium, potassium or trimethylammonium salt.

Following the procedure described in Example B-1 using in place of 1-(4-pyridinyl)-1,3-butanedione a molar equivalent quantity of the appropriate 1-Q-1,3-butanedione, it is contemplated that the following 1,2-dihydro-2-oxo-6-methyl-5-Q-3-pyridinecarbonitriles of Example B-2 thru B-9 can be obtained.

B-2. 1,2-Dihydro-2-oxo-6-methyl-5-(3-pyridinylcarbonyl)-3-pyridinecarbonitrile, using 1-(3-pyridinyl)-1,3-butanedione.

B-3. 1,2-Dihydro-2-oxo-6-methyl-5-(4-methyl-3-pyridinylcarbonyl)-3-pyridinecarbonitrile, using 1-(4-methyl-3-pyridinyl)-1,3-butanedione.

B-4. 1,2-Dihydro-2-oxo-6-methyl-5-(6-methyl-3-pyridinylcarbonyl)-3-pyridinecarbonitrile, using 1-(6-methyl-3-pyridinyl)-1,3-butanedione.

B-5. 1,2-Dihydro-2-oxo-6-methyl-5-(2,6-dimethyl-3-pyridinylcarbonyl)-3-pyridinecarbonitrile, using 1-(2,6-dimethyl-3-pyridinyl)-1,3-butanedione.

B-6. 1,2-Dihydro-2-oxo-6-methyl-5-(2-furanylcarbonyl)-3-pyridinecarbonitrile, using 1-(2-furanyl)-1,3-butanedione.

B-7. 1,2-Dihydro-2-oxo-6-methyl-5-(3-furanylcarbonyl)-3-pyridinecarbonitrile, using 1-(3-furanyl)-1,3-butanedione.

B-8. 1,2-Dihydro-2-oxo-6-methyl-5-(2-thienylcarbonyl)-3-pyridinylcarbonitrile, using 1-(2-thienyl)-1,3-butanedione.

B-9. 1,2-Dihydro-2-oxo-6-methyl-5-(3-thienylcarbonyl)-3-pyridinylcarbonitrile, using 1-(3-thienyl)-1,3-butanedione.

The compounds of formula I, e.g., examples A-1 through A-4 and B-1 through B-9, can be used as intermediates as illustrated by examples C-1 through C-4 and D-1 through D-25.

C.
5-(Q-CO)-6-[2-(DI-LOWER-ALKYLAMINO)ETHENYL]-2(1H)-PYRIDINONES

C-1. 6-[2-(Dimethylamino)ethenyl]-5-(2-furanylcarbonyl)-2(1H)-pyridinone—A mixture containing 30.5 g of 5-(2-furanylcarbonyl)-6-methyl-2(1H)-pyridinone, 400 ml of p-dioxane and 25 ml of dimethylformamide dimethyl acetal was heated under reflux for 6 hours and then allowed to cool. The separated crystalline product was collected, washed with isopropyl alcohol and dried in a vacuum oven at 80°–85° C. to yield 28.4 g of 6-[2-(dimethylamino)ethenyl]-5-(2-furanylcarbonyl)-2(1H)-pyridinone, m.p. 238°–240° C. with decomposition. The mother liquor on concentration yielded another 5.6 g of product.

C-2. 6-[2-(Dimethylamino)ethenyl]-5-(2-thienylcarbonyl)-2(1H)-pyridinone—To a mixture containing 57.8 g of 6-methyl-5-(2-thienylcarbonyl)-2(1H)-pyridinone in 400 ml of p-dioxane was added with stirring 62 g of bis(dimethylamino)-t-butoxymethane and the resulting reaction mixture was heated on a steam bath for 2 and ½ hours and then cooled. The separated product was collected, washed with isopropyl alcohol, dried in a vacuum oven at 90° C. to yield 70.1 g of 6-[2-(dimethylamino)ethenyl]-5-(2-thienylcarbonyl)-2(1H)-pyridinone, m.p. 248°–250° C.

Following the procedure described in Example C-1 using in place of 5-(2-furanylcarbonyl)-6-methyl-2(1H)-pyridinone a molar equivalent quantity of the appropriate 5-(Q-carbonyl)-6-methyl-2(1H)-pyridinone, it is contemplated that the 6-[2-(dimethylamino)ethenyl]-5-(Q-carbonyl)-2(1H)-pyridinones of Example C-3 and C-4 can be obtained.

C-3. 6-[2-(Dimethylamino)ethenyl]-5-(3-furanylcarbonyl)-2(1H)-pyridinone, using 5-(3-furanylcarbonyl)-6-methyl-2(1H)-pyridinone.

C-4. 6-[2-(Dimethylamino)ethenyl]-5-(3-thienylcarbonyl)-2(1H)-pyridinone, using 6-methyl-5-(3-thienylcarbonyl)-2(1H)-pyridinone.

D. 5-Q-1,6-NAPHTHYRIDIN-2(1H)-ONES

D-1. 5-(2-Furanyl)-1,6-naphthyridin-2(1H)-one—A mixture containing 20 g of 6-[2-(dimethylamino)ethenyl]5-(2-furanylcarbonyl)-2(1H)-pyridinone, 300 ml of dimethylformamide and 15.8 g of ammonium acetate was heated under reflux for 6 hours and then concentrated in vacuo. The residue was treated with 200 ml of boiling ethanol and the mixture chilled. The crystalline product was collected, washed with ethanol and dried in a vacuum oven at 80°–85° C. to yield 13.4 g of 5-(2-furanyl)-1,6-naphthyridin-2(1H)-one, m.p. >300° C.

Acid-addition salts of 5-(2-furanyl-1,6-naphthyridin-2(1H)-one are conveniently prepared by adding to a mixture of 2 g of 5-(2-furanyl)-1,6-naphthyridin-2(1H)-one in about 40 ml of aqueous methanol the appropriate acid, e.g. methanesulfonic acid, concentrated sulfuric acid, concentrated phosphoric acid, to a pH of about 2 to 3, chilling the mixture after partial evaporation and collecting the precipitate, e.g., dimethanesulphonate, sulphate, phosphate, respectively. Also, the acidaddition salt is conveniently prepared in aqueous solution by adding to water with stirring molar equivalent quantities of 5-(2-furanyl)-1,6-naphthyridin-2(1H)-one and the appropriate acid, e.g., lactic acid or hydrochloric acid, to prepare respectively the monolactate or monohydrochloride salt in aqueous solution.

Cationic salts of 5-(2-furanyl)-1,6-naphthyridin-2(1H)-one are conveniently prepared by reaction with an equivalent quantity of the appropriate base, for example, sodium hydroxide, potassium hydroxide or trimethylammonium hydroxide, to produce the corresponding respective sodium, potassium or trimethylammonium salt. The salts are prepared in solution or in solid form by suspending equivalent quantities of 5-(2-furanyl)-1,6-naphthyridin-2(1H)-one and base in water or water-methanol to form the solution of the salt or by evaporating the solvent from the solution to obtain the salt in solid form.

D-2. 5-(2-Thienyl)-1,6-naphthyridin-2(1H)-one—A mixture containing 49 g of 6-[2-(dimethylamino)ethenyl]5-(2-thienylcarbonyl)-2(1H)-pyridinone, 250 ml of dimethylformamide and 27.5 g of ammonium acetate was refluxed with stirring for two hours, allowed to cool and then concentrated on a rotary evaporator with stirring. The residue was slurried with water and the solid was collected, washed with water and dried in a vacuum oven at 90° C. to yield 40 g of 5-(2-thienyl)-1,6-napthyridin-2(1H)-one, m.p. 238°–240° C.

Acid-addition and cationic salts of 5-(2-thienyl)-1,6-naphthyridin-2(1H)-one are conveniently prepared following the procedure described for preparing the corresponding acid-addition and cationic salts in Example D-1.

D-3. 1,2-Dihydro-2-oxo-5-(4-pyridinyl)-1,6-naphthyridine-3-carbonitrile—A mixture containing 14 g of 1,2-dihydro-2-oxo-6-methyl-5-(4-pyridinylcarbonyl)-3-pyridinecarbonitrile, 100 ml of dimethylformamide and 10 ml of dimethylformamide dimethyl acetal was gently heated at 50°–55° C. with stirring for five hours and then allowed to stand at room temperature overnight (about 15 hours). The reaction mixture containing 6-[2-(dimethylamino)ethenyl]-1,2-dihydro-2-oxo-5-(4-pyridinylcarbonyl)-3-pyridinecarbonitrile (some separated as crystals and some in solution) was treated with 10.5 g of ammonium acetate and the mixture refluxed for five hours and then allowed to cool to room temperature. The separated solid was collected, washed with dimethylformamide and dried in a vacuum oven at 90°–95° C. to produce 8.4 g of 1,2-dihydro-2-oxo-5-(4-pyridinyl)-1,6-naphthyridine-3-carbonitrile, m.p. >300° C. Concentration of the mother liquor yielded another 3.4 g of product.

D-4. 1,2-Dihydro-2-oxo-5-(4-pyridinyl)-1,6-naphthyridine-3-carboxylic Acid—A mixture containing 15 g of 1,2-dihydro-2-oxo-5-(4-pyridinyl)-1,6-naphthyridine-3-carbonitrile and the 60 ml of 90% sulphuric acid was refluxed overnight (about 15 hours), cooled and poured onto ice. The aqueous mixture was neutralized by adding aqueous ammonium hydroxide solution. The separated solid was collected, washed with water and then dried in a vacuum oven at 90°–95° C. to produce 9.2 g of 1,2-dihydro-2-oxo-5-(4-pyridinyl)-1,6-naphthyridine-3-carboxylic acid as its hydrate (4:1), m.p. >300° C.

D-5. 5-(4-Pyridinyl)-1,6-napthyridin-2(1H)-one—A 9.4 g portion of 1,2-dihydro-2-oxo-5-(4-pyridinyl)-1,6-naphthyridin-3-carboxylic acid hydrate (4:1) was divided roughly into four equal parts in four test tubes. Silicone oil was heated in a 3-necked 250 ml round bottom flask using a heating mantle to 370°–375° C. Each test tube containing the acid was suspended in the heated oil and was taken out as soon as all of the compound had melted and decarboxylated to give a dark oil (about two minutes). The dark oil was immediately treated with about 5 ml of dimethylformamide to avoid rock-like solidification. The contents of the tubes were transferred to a 500 ml flask by washing with dimethylformamide. More dimethylformamide was added, the total volume of about 300 ml, the mixture heated to reflux and then filtered. The filtrate was concentrated to dryness on a rotary evaporator. The residue was dissolved in 100 ml of 5% aqueous sodium hydroxide solution, the solution treated with decolorizing charcoal and filtered. The clear yellow filtrate was acidified with acetic acid and the resulting light yellow precipitate was collected, washed with water, dried in a vacuum oven at 90°–95° C., recrystallized from dimethylformamide and dried at 90°–95° C. to yield 5.6 g of 5-(4-pyridinyl)-1,6-naphthyridin-2(1H)-one, m.p. >300° C.

Acid-addition salts of 5-(4-pyridinyl)-1,6-naphthyridin-2(1H)-one are conveniently prepared following the procedure described for preparing the corresponding acid-addition salts in Example D-1.

Following the procedure described in D-1 using in place of 6-[2-(dimethylamino)ethenyl]-5-(2-furanylcarbonyl)-2(1H)-pyridinone a molar equivalent quantity of the appropriate 5-(Q-CO)-6-[2-(dimethylamino)ethenyl]-2(1H)-pyridinone, it is contemplated that the corresponding 5-Q-1,6-naphthyridin-2(1H)-ones of Examples D-6 and D-7 can be obtained.

D-6. 5-(3-Furanyl)-1,6-naphthyridin-2(1H)-one, using 6-[2-(dimethylamino)ethenyl]-5-(3-furanylcarbonyl)-2(1H)-pyridinone.

D-7. 5-(3-Thienyl)-1,6-naphthyridin-2(1H)-one, using 6-[2-(dimethylamino)ethenyl]-5-(2-thienylcarbonyl)-2(1H)-pyridinone.

Following the procedure described in Example D-3 using in place of 1,2-dihydro-2-oxo-6-methyl-5-(4-pyridinylcarbonyl)-3-pyridinecarbonitrile a molar equivalent quantity of the appropriate 1,2-dihydro-5-(Q-CO)-6-methyl-2-oxonicotinonitrile, it is contemplated that the corresponding 1,2-dihydro-2-oxo-5-Q-1,6-naphthyridine-3-carbonitriles of Example D-8 thru D-13 can be obtained.

D-8. 1,2-Dihydro-2-oxo-5-(3-pyridinyl)-1,6-naphthyridine-3-carbonitrile, using 1,2-dihydro-2-oxo-6-methyl-5-(3-pyridinylcarbonyl)-3-pyridinecarbonitrile.

D-9. 1,2-Dihydro-2-oxo-5-(4-methyl-3-pyridinyl)-1,6-naphthyridine-3-carbonitrile, using 1,2-dihydro-2-oxo-6-methyl-5-(4-methyl-3-pyridinylcarbonyl)-3-pyridinecarbonitrile.

D-10. 1,2-Dihydro-2-oxo-5-(6-methyl-3-pyridinyl)-1,6-naphthyridine-3-carbonitrile, using 1,2-dihydro-6-oxo-6-methyl-5-(6-methyl-3-pyridinylcarbonyl)-3-pyridinecarbonitrile.

D-11. 1,2-Dihydro-2-oxo-5-(2,6-dimethyl-3-pyridinyl)-1,6-naphthyridine-3-carbonitrile, using 1,2-dihydro-2-oxo-6-methyl-5-(2,6-dimethyl-3-pyridinylcarbonyl)-3-pyridinecarbonitrile.

D-12. 1,2-Dihydro-2-oxo-5-(2-furanyl)-1,6-naphthyridine-3-carbonitrile, using 1,2-dihydro-2-oxo-6-methyl-5-(2-furanylcarbonyl)-3-pyridinecarbonitrile.

D-13. 1,2-Dihydro-2-oxo-5-(2-thienyl)-1,6-naphthyridine-3-carbonitrile, using 1,2-dihydro-2-oxo-6-methyl-5-(2-thienylcarbonyl)-3-pyridinecarbonitrile.

Following the procedure described in Example D-4 using in place of 1,2-dihydro-2-oxo-5-(4-pyridinyl)-1,6-naphthyridine-3-carbonitrile a corresponding molar equivalent quantity of the appropriate 1,2-dihydro-2-oxo-5-Q-1,6-naphthyridine-3-carbonitrile, it is contemplated that the corresponding 1,2-dihydro-2-oxo-5-Q-1,6-naphthyridine-3-carboxylic acids of Examples D-14 thru D-19 can be obtained.

D-14. 1,2-Dihydro-2-oxo-5-(3-pyridinyl)-1,6-naphthyridine-3-carboxylic acid, using 1,2-dihydro-2-oxo-5-(3-pyridinyl)-1,6-naphthyridin-3-carbonitrile.

D-15. 1,2-Dihydro-2-oxo-5-(4-methyl-3-pyridinyl)-1,6-naphthyridine-3-carboxylic acid, using 1,2-dihydro-2-oxo-5-(4-methyl-3-pyridinyl)-1,6-naphthyridin-3-carbonitrile.

D-16. 1,2-Dihydro-2-oxo-5-(6-methyl-3-pyridinyl)-1,6-naphthyridine-3-carboxylic acid, using 1,2-dihydro-2-oxo-5-(6-methyl-3-pyridinyl)-1,6-naphthyridin-3-carbonitrile.

D-17. 1,2-Dihydro-2-oxo-5-(2,6-dimethyl-3-pyridinyl)-1,6-naphthyridine-3-carboxylic acid, using 1,2-dihydro-2-oxo-5-(2,6-dimethyl-3-pyridinyl)-1,6-naphthyridin-3-carbonitrile.

D-18. 1,2-Dihydro-2-oxo-5-(2-furanyl)-1,6-naphthyridine-3-carboxylic acid, using 1,2-dihyro-2-oxo-5-(2-furanyl)-1,6-naphthyridin-3-carbonitrile.

D-19. 1,2-Dihydro-2-oxo-5-(2-thienyl)-1,6-naphthyridine-3-carboxylic acid, using 1,2-dihydro-2-oxo-5-(2-thienyl)-1,6-naphthyridin-3-carbonitrile.

Following the procedure described in Example D-5 but using in place of 1,2-dihydro-2-oxo-5-(4-pyridinyl)-1,6-naphthyridine-3-carboxylic acid the appropriate 1,2-dihydro-2-oxo-5-Q-1,6-napthyridine-3-carboxylic acid, it is contemplated that the corresponding 5-Q-1,6-naphthyridine-2(1H)-ones of Examples D-20 thru D-25 can be obtained.

D-20. 5-(3-Pyridinyl)-1,6-naphthyridin-2(1H)-one, using 1,2-dihydro-2-oxo-5-(3-pyridinyl)-1,6-naphthyridine-3-carboxylic acid.

D-21. 5-(4-Methyl-3-pyridinyl)-1,6-naphthyridin-(1H)-one, using 1,2-dihydro-2-oxo-5-(4-methyl-3-pyridinyl)-1,6-naphthyridin-3-carboxylic acid.

D-22. 5-(6-Methyl-3-pyridinyl)-1,6-naphthyridin-2(1H)-one, using 1,2-dihydro-2-oxo-5-(6-methyl-3-pyridinyl)-1,6-naphthyridine-3-carboxylic acid.

D-23. 5-(2,6-Dimethyl-3-pyridinyl)-1,6-naphthyridin-2(1H)-one, using 1,2-dihydro-2-oxo-5-(2,6-dimethylpyridinyl)-1,6-naphthyridin-3-carboxylic acid.

D-24. 5-(2-Furanyl)-1,6-naphthyridin-2(1H)-one, using 1,2-dihydro-2-oxo-5-(2-furanyl)-1,6-naphthyridine-3-carboxylic acid.

D-25. 5-(2-Thienyl)-1,6-naphthyridin-2(1H)-one, using 1,2-dihydro-2-oxo-5-(2-thienyl)-1,6-naphthyridine-3-carboxylic acid.

The usefulness of the compounds of formula I as cardiotonic agents is demonstrated by their effectiveness in standard pharmacological test procedures, for example, in causing a significant increase in contractile force of the isolated cat or guinea pig atria and papillary muscle and/or in causing a significant increase in cardiac contractile force in the anesthetized dog with lower or minimal changes in heart rate and blood pressure. Detailed descriptions of these test procedures appear in U.S. Pat. No. 4,072,746, issued Feb. 7, 1980.

Cardiotonic activity in said isolated cat or guinea pig atria and papillary muscle procedure, is indicated by a significant increase, that is, greater than 25% (cat) or 30% (g.pig) in papillary muscle force and a significant increase, that is, greater than 25% (cat) or 30% (g.pig) in right atrial force, with a lower percentage increase (about one-half or less than the percentage increase in right atrial force or papillary muscle force) in right atrial rate. Because of the lower control active tensions of guinea pig tissues, the percent change from control values of both rate and force responses is elevated slightly, i.e., 5%. Thus, whereas cardiotonic activity is ascertained with a papillary muscle force or right atrial force increase of 26% and greater in the cat test, corresponding activity in the guinea pig test is designated with a papillary muscle force (PMF) or right atrial force (RAF) increase of 31% or greater. Representative examples of the compounds of Formula I were tested by said guinea pig atria and papillary muscle procedure with the following results:

| Example | Dose µg/ml | % Change from Control RAF | PMF |
|---|---|---|---|
| A-1 | 30 | 61 | 55 |
|  | 100 | 245 | 84 |
| A-2 | 30 | 82 | 47 |
|  | 100 | 297 | 133 |
| B-1 | 30 | 36 | 20 |
|  | 100 | 218 | 62 |

The present invention includes within its scope a cardiotonic composition for increasing cardiac contractility, said composition comprising a pharmaceutically acceptable carrier and, as the active component thereof, the compound of formula I or pharmaceutically acceptable or acid-addition or cationic salt thereof. The invention also includes within its scope the method for increasing cardiac contractility in a patient requiring such treatment which comprises administering to such patient a cardiotonically effective amount of said cardiotonically active compound of formula I. In clinical practice said compound will normally be administered orally or parenterally in a wide variety of dosage forms.

Solid compositions for oral administration include compressed tablets, pills, powders and granules. In such solid compositions, at least one of the active compounds is admixed with at least one inert diluent such as starch, calcium carbonate, sucrose or lactose. These compositions may also contain additional substances other than inert diluents, e.g., lubricating agents, such as magnesium stearate, talc, and the like.

Liquid compositions for oral administration include pharmaceutically acceptable emulsions, solutions, suspensions, syrups and elixirs containing inert diluents commonly used in the art, such as water and liquid paraffin. Besides inert diluents such compositions may also contain adjuvants, such as wetting and suspending agents, and sweetening, flavoring, perfuming and preserving agents. According to the invention, the compounds for oral administration also include capsules of absorbable material, such as gelatin, containing said active component with or without the addition of diluents or excipients.

Preparations according to the invention for parenteral administration include sterile aqueous, aqueousorganic, and organic solutions, suspensions and emulsions. Examples of organic solvents or suspending media are propylene glycol, polyethylene glycol, vegetable oils such as olive oil and injectable organic ester such as ethyl oleate. These compositions can also contain adjuvants such as stablilizing, preserving, wetting, emulsifying and dispersing agents.

They can be sterilized, for example by filtration through a bacterial-retaining filter, by incorporation of sterilizing agents in the compositions, by irradiation or by heating. They can also be manufactured in the form of sterile solid compositions which can be dissolved in sterile water or some other sterile injectable medium immediately before use.

The percentage of active component in the said composition and method for increasing cardiac contractility can be varied so that a suitable dosage is obtained. The dosage administered to a particular patient is variable, depending upon the clinician's judgement using as the criteria: the route of administration, the duration of treatment, the size and condition of the patient, the potency of the active component and the patient's response thereto. An effective dosage amount of active component can thus only be determined by the clinician considering all criteria and utilizing his best judgement on the patient's behalf.

We claim:

1. 3-Z-5-(Q-CO)-6-methyl-2-(1H)-pyridinone having the formula I

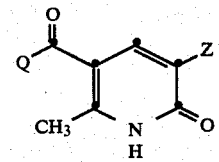

or pharmaceutically acceptable cationic salt thereof, where Q is 2(or 3)-furanyl or 2(or 3)-thienyl when Z is hydrogen or where Q is 4(or 3)-pyridinyl when Z is cyano, or acid addition salt thereof where Q is 4(or 3)-pyridinyl.

2. 5-(2-Furanylcarbonyl)-6-methyl-2(1H)-pyridinone according to claim 1.

3. 6-Methyl-5-(2-thienylcarbonyl)-2(1H)-pyridinone according to claim 1.

4. 1,2-Dihydro-2-oxo-5-(4-pyridinylcarbonyl)-6-methyl-3-pyridinecarbonitrile according to claim 1.

5. A cardiotonic composition for increasing cardiac contractility which comprises a pharmaceutically acceptable carrier and, as the active component thereof, a cardiotonically effective amount of 3-Z-5-(Q-CO)-6-methyl-2(1H)-pyridinone according to claim 1 or pharmaceutically acceptable acid-addition or cationic salt thereof.

6. A cardiotonic composition according to claim 5 where the active component is 5-(2-furanylcarbonyl)-6-methyl-2(1H)-pyridinone.

7. A cardiotonic composition according to claim 5 where the active component is 6-methyl-5-(2-thienylcarbonyl)-2(1H)-pyridinone.

8. A cardiotonic composition according to claim 5 where the active component is 1,2-dihydro-2-oxo-6-methyl-5-(4-pyridinylcarbonyl)pyridine-3-carbonitrile.

9. A method for increasing cardiac contractility in a patient requiring such treatment which comprises administering orally or parenterally in a solid or liquid dosage form to such patient a cardiotonically effective amount of 3-Z-5-(Q-CO)-6-methyl-2(1H)-pyridinone according to claim 1, or pharmaceutically acceptable acid-addition or cationic salt thereof.

10. A method according to claim 9 where the active component is 5-(2-furanylcarbonyl)-6-methyl-2(1H)-pyridinone.

11. A method according to claim 9 where the active component is 6-methyl-5-(2-thienylcarbonyl)-2(1H)-pyridinone.

12. A method according to claim 9 where the active component is 1,2-dihydro-2-oxo-6-methyl-5-(4-pyridinyl)-pyridine-3-carbonitrile.

* * * * *